United States Patent [19]

Iovanna et al.

[11] Patent Number: 5,436,169
[45] Date of Patent: Jul. 25, 1995

[54] PROTEIN ASSOCIATED WITH ACUTE PANCREATITIS AGENTS FOR THE SCREENING OF ACUTE PANCREATITIS

[75] Inventors: Juan-Lucio Iovanna, Marseille; Keim Volker, Heddesheim; Jean-Charles Dagorn, Marseille, all of France

[73] Assignee: Institut National de la Sante et de la Recherche Medicale, Paris Cedex, France

[21] Appl. No.: 778,156
[22] PCT Filed: Apr. 18, 1991
[86] PCT No.: PCT/FR91/00323
  § 371 Date: Dec. 19, 1991
  § 102(e) Date: Dec. 19, 1991
[87] PCT Pub. No.: WO91/16428
  PCT Pub. Date: Oct. 31, 1991

[30] Foreign Application Priority Data

Apr. 20, 1990 [FR] France .................. 90 05062

[51] Int. Cl.⁶ ............... G01N 33/532; G01N 33/53; C07K 16/44
[52] U.S. Cl. ................... 436/518; 436/536; 436/549; 436/811; 435/7.1; 435/7.92; 435/810; 530/387.1; 530/387.9; 530/379.3; 530/391.3
[58] Field of Search ............ 435/7.1, 240.27; 436/518, 536, 548, 547, 808; 530/387.9, 388.1, 389.1, 389.3, 391.3

[56] References Cited

U.S. PATENT DOCUMENTS

4,948,723 8/1990 Hermon-Taylor et al. ......... 435/7.1

FOREIGN PATENT DOCUMENTS

286114 12/1988 European Pat. Off. .

OTHER PUBLICATIONS

Terazono et al., *J. Biol. Chem.*, vol. 263, pp. 2111–2114 (1988).
Rowini et al., *FEBS Lett.*, vol. 229, pp. 171–174 (1988).
Goldenberg et al., in *Cancer imaging with radiolabeled antibodies*, (1990), ed. David M. Goldenberg, Kluwer Academic Publishers, pp. 273–292.
Scheele, *The Exocrine Pancreas: Biology, Pathobiology and Diseases*, V. L. W. Go et al., Eds., Raven Press, N.Y., pp. 185–192 (1986).
Giorgi et al., *J. Clin. Invest.*, vol. 84, pp. 100–106 (1989).
Maniatis, "Molecular Cloning—A Laboratory Manual Second Edition"—Cold Spring Harbor Laboratory Press, 1989, in particular p. 18.7.
Gastroenterology, vol. 100, No. 3, Mar. 1991, pp. 755–782; Keim, V., et al.: "Characterization of a rat pancreatic secretory protein associated with pancreatitis".
Gastroenterology, vol. 98, No. 5pt2, May 1990, p. A220, Iovanna, J. et al.: "Rat Pancreatitis-Associated Protein (PAP) messenger RNA, nucleaotide sequence and expression during acute experimental pancreatitis".
Digestion, vol. 31, No. 3, 25 Sep. 1985, pp. 191, Keim, V. et al.: "Pancreatitis-Associated Protein (PAP) in cerulein and bile acid induced ex".
Digestive Diseases and Sciences, vol. 30, No. 10, Oct. 1985, p. 977, Keim, V. & Rohr, G.: "Pancreatitis-Associated Proteins (PAP) in cerulein- and bile acid-induced p".
Digestive Diseases and Sciences, vol. No. 10, Oct. 1985, pp. 988, Rohr, G. et al.: "Appearance of Pancreatitis Associated Protein (PAP) in taurocholate pancreatitis in the rat demonstrate by immuno-histology and immuno-electomicroscopy".
Digestion, vol. 29, 1984, pp. 242–249; Keim, et al.: "An additional secretory protein in the rate pancreas".
Clin. Physiol. Biochem., vol. 4, 1986, pp. 136–142; Keim, V.: "Pancreatitis-associated protein in bile acid-induced pancreatitis of the rat".

*Primary Examiner*—Toni R. Scheiner
*Assistant Examiner*—Nancy J. Parsons
*Attorney, Agent, or Firm*—Oblon, Spivak, McClelland, Maier & Neustadt

[57] ABSTRACT

The invention relates to the family of the protein (PAP) associated with acute pancreatitis in man and in the rat. It also relates to the nucleotide fragments coding for the above proteins.

Also included in the framework of the invention are antibodies which recognize the PAP and which are capable of being used for the purpose of diagnosing pancreatitis.

The invention also relates to the production of the PAP, in particular by genetic engineering.

5 Claims, 6 Drawing Sheets

FIG. 1A
PAP
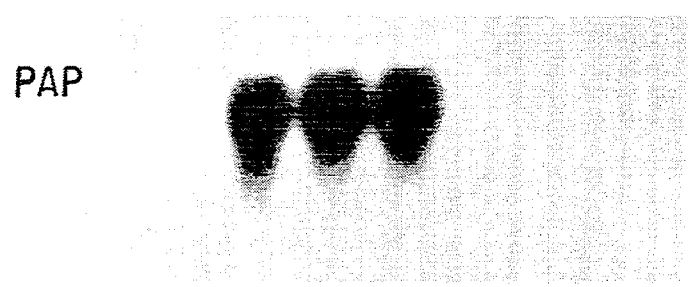
Am
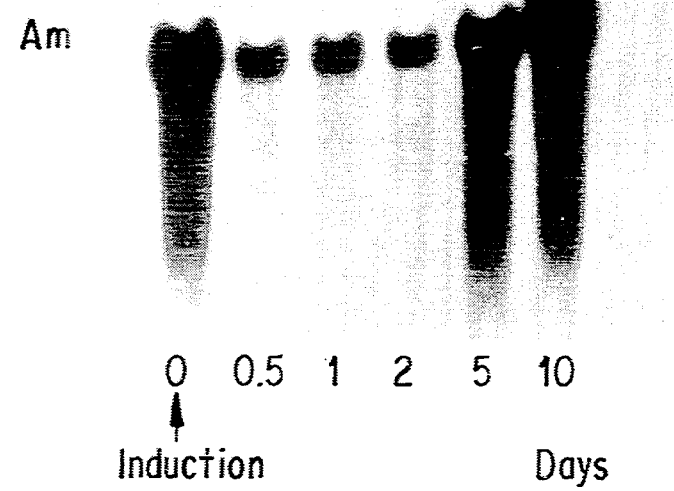
0  0.5  1  2    5   10
↑                    Days
Induction
FIG. 1B

```
AAAACCATCCAAATCGCCCGCAAGACAGCTAAGGAGGAGCAGAAAGATGATG   52

AGAGTTAAT ATG TTG CAT CGC TTG GCC TTC CCA GTC ATG      91
          Met Leu His Arg Leu Ala Phe Pro Val Met

TCC TGG ATG CTG CTC TCC TGC CTG ATG CTC TTA TCA CAG    130
Ser Trp Met Leu Leu Ser Cys Leu Met Leu Leu Ser Gln

GTG CAA GGA GAA GAC TCT CCG AAG AAA ATA CCC TCT GCA    169
Val Gln Gly Glu Asp Ser Pro Lys Lys Ile Pro Ser Ala

CGC ATT AGT TGC CCC AAA GGC TCC CAG GCA TAT GGC TCC    208
Arg Ile Ser Cys Pro Lys Gly Ser Gln Ala Tyr Gly Ser

TAC TGC TAT GCC CTG TTT CAG ATA CCA CAG ACC TGG TTT    247
Tyr Cys Tyr Ala Leu Phe Gln Ile Pro Gln Thr Trp Phe

GAT GCA GAA CTG GCC TGC CAG AAG AGA CCT GAA GGA CAC    286
Asp Ala Glu Leu Ala Cys Gln Lys Arg Pro Glu Gly His

CTT GTA TCT GTG CTC AAT GTA GCT GAA GCT TCA TTC TTG    325
Leu Val Ser Val Leu Asn Val Ala Glu Ala Ser Phe Leu

GCA TCC ATG GTC AAG AAC ACT GGA AAC AGC TAC CAA TAT    364
Ala Ser Met Val Lys Asn Thr Gly Asn Ser Tyr Gln Tyr

ACC TGG ATT GGA CTC CAT GAC CCC ACT CTT GGT GGA GAA    403
Thr Trp Ile Gly Leu His Asp Pro Thr Leu Gly Gly Glu

CCC AAT GGA GGT GGA TGG GAG TGG AGT AAC AAT GAC ATA    442
Pro Asn Gly Gly Gly Trp Glu Trp Ser Asn Asn Asp Ile

ATG AAT TAT GTC AAC TGG GAG AGG AAC CCA TCT ACT GCC    481
Met Asn Tyr Val Asn Trp Glu Arg Asn Pro Ser Thr Ala

TTA GAC CGC GGA TTC TGT GGC AGC TTG TCA AGA TCT TCT    520
Leu Asp Arg Gly Phe Cys Gly Ser Leu Ser Arg Ser Ser
```

FIG.2A

```
GGA TTT CTA AGA TGG AGA GAT ACC ACA TGT GAA GTT GAA   559
Gly Phe Leu Arg Trp Arg Asp Thr Thr Cys Glu Val Glu

GTT GCC CTA CGT CTG CAA ATT TAC AGG TTA AAA TTA CCA   598
Val Ala Leu Arg Leu Gln Ile Tyr Arg Leu Lys Leu Pro

GAC AGC AAA CAG CTT T AGTTTGTCCTGAAGCACATCCTGTCAAGGG  644
Asp Ser Lys Gln Leu

GCAAAATATGAAGACTTGCGTAGAAAAAGTGTATTCTATCTACAGTCCATAT  696

TGGAGCTCTAATCATTCTTTAGCCAATTTTGTATAAGTTGTGTCCTCATGTC  748

TTGGAAAGCAGTAATAAACCTCAGTCTCTCTTCGAAAAAAAAAAA         793
```

FIG.2B

```
TTT GTT AAG GAT TCC CTT GAG AAT TAT GTA AAA GTT TTA    39
Phe Val Lys Asp Ser Leu Glu Asn Tyr Val Lys Val Leu    13

CAA GAG TCC ATC TCA TTC TCT TTG TCC CCC TCA AAG CTG    78
Gln Glu Ser Ile Ser Phe Ser Leu Ser Pro Ser Lys Leu    26

GCT TGC CAG AAG CGG CCC TCT GGA AAA CTG GTG TCT GTG   117
Ala Cys Gln Lys Arg Pro Ser Gly Lys Leu Val Ser Val    39

CTC AGT GGG GCT GAG GGA TCC TTC GTG TCC TCC CTG GTG   156
Leu Ser Gly Ala Glu Gly Ser Phe Val Ser Ser Leu Val    52

AGG AGC ATT AGT AAC AGC TAC TCA TAC ATC TGG ATT GGG   195
Arg Ser Ile Ser Asn Ser Tyr Ser Tyr Ile Trp Ile Gly    65

CTC CAT GAC CCC ACA CAG GTG CGA GTA TAT CCT CCC CTC   234
Leu His Asp Pro Thr Gln Val Arg Val Tyr Pro Pro Leu    78

TCT GTT ACC TCT CAA GGT ACT GTT GTT GCC CAG GCG CAC   273
Ser Val Thr Ser Gln Gly Thr Val Val Ala Gln Ala His    91

TCC CTG TCC CCA GTC CCT GCC CAG GAA GTA CTT           306
Ser Leu Ser Pro Val Pro Ala Gln Glu Val Leu          102
```

FIG.3

```
           cgggagagtgactcctgattgcctcctcaagtcgcagacact ATG CTG   48
                                                     Met Leu    2

CCT CCC ATG GCC CTG CCC AGT GTA TCT TGG ATG CTG CTT            87
Pro Pro Met Ala Leu Pro Ser Val Ser Trp Met Leu Leu            15

TCC TGC CTC ATG CTG CTG TCT CAG GTT CAA GGT GAA GAA           126
Ser Cys Leu Met Leu Leu Ser Gln Val Gln Gly Glu Glu            28

CCC CAG AGG GAA CTG CCC TCT GCA CGG ATC CGC TGT CCC           165
Pro Gln Arg Glu Leu Pro Ser Ala Arg Ile Arg Cys Pro            41

AAA GGC TCC AAG GCC TAT GGC TCC CAC TGC TAT GCC TTG           204
Lys Gly Ser Lys Ala Tyr Gly Ser His Cys Tyr Ala Leu            54

TTT TTG TCA CCA AAA TCC TGG ACA GAT GCA GAT CTG GCC           243
Phe Leu Ser Pro Lys Ser Trp Thr Asp Ala Asp Leu Ala            67

TGC CAG AAG CGG CCC TCT GGA AAC CTG GTG TCT GTG CTC           282
Cys Gln Lys Arg Pro Ser Gly Asn Leu Val Ser Val Leu            80

AGT GGG GCT GAG GGA TCC TTC GTG TCC TCC CTG GTG AAG           321
Ser Gly Ala Glu Gly Ser Phe Val Ser Ser Leu Val Lys            93

AGC ATT GGT AAC AGC TAC TCA TAC GTC TGG ATT GGG CTC           360
Ser Ile Gly Asn Ser Tyr Ser Tyr Val Trp Ile Gly Leu           106

CAT GAC CCC ACA CAG GGC ACC GAG CCC AAT GGA GAA GGT           399
His Asp Pro Thr Gln Gly Thr Glu Pro Asn Gly Glu Gly           119

TGG GAG TGG AGT AGC AGT GAT GTG ATG AAT TAC TTT GCA           438
Trp Glu Trp Ser Ser Ser Asp Val Met Asn Tyr Phe Ala           132

TGG GAG AGA AAT CCC TCC ACC ATC TCA AGC CCC GGC CAC           477
Trp Glu Arg Asn Pro Ser Thr Ile Ser Ser Pro Gly His           145

TGT GCG AGC CTG TCC AGA AGC ACA GCA TTT CTG AGG TGG           516
Cys Ala Ser Leu Ser Arg Ser Thr Ala Phe Leu Arg Trp           158
```

FIG.4A

```
AAA GAT TAT AAC TGT AAT GTG AGG TTA CCC TAT GTC TGC   555
Lys Asp Tyr Asn Cys Asn Val Arg Leu Pro Tyr Val Cys   171

AAA GTT CAC   tgactagtgcaggagggaagtcagcagcctgtgtttggt  603
Lys Val His                                            174 gtgcaactcatcatgggcatgagaccagtgtgaggactcaccctggaagaga  655 atattcgcttaattcccccaacctgaccacctcattcttatctttcttctgt  707 ttcttcctccccgctagtcatttcagtctcttcattttgtcatacggcctaa  759 ggctttaaagagcaataaaattttttagtctgcaaaaaaa              798
```

FIG. 4B

PROTEIN ASSOCIATED WITH ACUTE PANCREATITIS AGENTS FOR THE SCREENING OF ACUTE PANCREATITIS

The present invention relates to proteins associated with acute pancreatitis and agents for the diagnosis of this disease.

Acute pancreatitis is an inflammatory disease of the pancreas which, pathologically speaking, extends from the simple edematous form to the complete hemorrhagic necrosis of the gland. Necrohemorrhagic hepatitis is a very serious disease since, depending on the authors, its mortality is estimated to vary from 30 to 70%. In certain cases it is very difficult to establish the diagnosis of acute pancreatitis with certainty (Sarner, M. et al, Gastroenterol. (1984), 13: 865-870). This diagnosis is based in particular on clinical examination (acute abdominal pain), on the determination of a certain number of substances in the plasma or in the peritoneal fluid (Bradley, J. et al., Br. J. Surg. (1981), 68: 245-246; and Dubick, M. et al., Dig. Dis. Sci. (1987), 32: 305-312). The analytical determinations employed include those for amylase, lipase, trypsin, elastase, ribonuclease, phospholipase A2, $\alpha$-2 macroglobulin, calcium, LDH, protease inhibitors and others. However, none of them has proved to be specific, practical or above all, discriminating. Hence, it is usually considered sufficient to determine amylasemia. Recently, ultrasonography and computerized tomography have appeared to be able to facilitate the diagnosis of pancreatitis without, however, decisive progress being made (Silverstein, W. et al., Am. J. Roentgenol., (1981), 137: 497-502).

In 1984, Keim et al. published (Digestion, (1984), 29: 242-249) results of the consequences of cannulation of the pancreatic duct and the induction of pancreatitis on the protein composition of the pancreatic juice in the rat, this animal being used as an experimental model. After the operation of cannulation (1 to 2 days later), the authors observed a fall in the level of amylase in the pancreatic juice followed, 3 to 4 days after the operation, by a return to the normal amylase level.

Separation of the proteins of the pancreatic juice during this period of remission by means of electrophoresis on polyacrylamide gel (PAGE) showed an additional protein band, detectable as early as 12 hours after the operation and as late as 3 to 4 days after the operation. This protein band did not exist in the untreated control rat. This secretory protein has been called PAP ("pancreatitis-associated protein").

Subsequently, Keim et al. carried out measurements of the amount of PAP present in the pancreatic tissue of the rat, after induction of pancreatitis, by means of tests involving the detection of complement binding.

However, up to now these tests have not made it possible to detect the existence of the PAP in the serum of the rat in which pancreatitis has been induced.

The agents hitherto suggested in the prior art had thus not enabled an adequate identification of the PAP protein in the rat, which raises the question as to the relevance of an investigation in man in order to investigate whether such a protein can be detected.

Furthermore, the results available up to now have not made it possible to estimate the usefulness of PAP for carrying out a diagnosis of pancreatitis.

The inventors have observed that rat polyclonal antibodies which recognize the rat PAP protein do not show significant recognition of a protein in human serum.

Thus, after making this observation, the inventors investigated a more adequate identification of the rat PAP protein, with a view to defining tools of investigation in man: the inventors have now clearly identified the PAP protein in the rat and have determined its amino acid sequence. On the basis of these results, they have developed agents which should make it possible to detect and identify whether a protein corresponding to rat PAP exists in man.

The cloning and sequencing of the PAP messenger RNA starting from a library of rat pancreatic cDNAs has also made it possible to demonstrate unambiguously that the PAP is indeed synthesized by the pancreas. The inventors have also shown that the protein is very weakly expressed in the absence of pancreatic inflammation and strongly expressed during pancreatitis.

In view of the frailty of the patients suffering from pancreatitis, it was out of the question to consider collecting the pancreatic juice from such patients in order to look for the possible presence there of a human PAP protein (PAP-H).

The inventors have screened a human pancreatic cDNA bank with the aid of a cDNA clone obtained beforehand and corresponding to the rat PAP.

The inventors have succeeded in isolating different clones containing fragments of cDNA capable of hybridizing with the cDNA of the rat PAP, as is described hereafter.

Hence, the present invention relates to cDNA fragments capable of coding for the rat PAP protein as well as to cDNA fragments capable of coding for the proteins of the family of the human PAP. The invention also relates to the proteins encoded by these cDNA fragments.

It also relates to vectors modified by integration of the above-mentioned cDNA fragments, in particular for the expression of these fragments.

The invention also relates to monoclonal or polyclonal antibodies directed against the PAP protein, in particular against the human PAP, as well as to their use in procedures making use of medical imaging, or as agent for the diagnosis of acute pancreatitis in kits and in vitro diagnostic procedures.

A first family of DNA fragments according to the invention thus includes the cDNA fragments coding for the rat PAP.

Belonging to this family are cDNA fragments characterized in that they correspond to the following S1 nucleotide sequence (SEQ ID NO: 1) coding for the rat PAP protein, to a part or a variant of this sequence in the case in which this part or variant codes for a protein or a peptide recognized by antibodies directed against the rat PAP protein, or which hybridizes with the S1 sequence in a hybridization solution containing 6×SSC, 5×Denhardt, 0.5% SDS, 10 mM EDTA, 200 μg salmon sperm DNA, for 18 hours at 68° C. and after rinsing under the following conditions: 6×SSC, 0.1% SDS, twice for 15 minutes at 65° C.

Sequence S1:

| 10 | 20 | 30 | 40 | 50 | 60 |
|---|---|---|---|---|---|
| AAAACCATCC | AAATCGCCCG | CAAGACAGCT | AAGGAGGAGC | AGAAAGATGA | TGAGAGTTAA |
| 70 | 80 | 90 | 100 | 110 | 120 |
| TATGTTGCAT | CGCTTGGCCT | TCCCAGTCAT | GTCCTGGATG | CTGCTCTCCT | GCCTGATGCT |
| 130 | 140 | 150 | 160 | 170 | 180 |
| CTTATCACAG | GTGCAAGGAG | AAGACTCTCC | GAAGAAATA | CCCTCTGCAC | GCATTAGTTG |
| 190 | 200 | 210 | 220 | 230 | 240 |
| CCCCAAAGGC | TCCCAGGCAT | ATGGCTCCTA | CTGCTATGCC | CTGTTTCAGA | TACCACAGAC |
| 250 | 260 | 270 | 280 | 290 | 300 |
| CTGGTTTGAT | GCAGAACTGG | CCTGCCAGAA | GAGACCTGAA | GGACACCTTG | TATCTGTGCT |
| 310 | 320 | 330 | 340 | 350 | 360 |
| CAATGTAGCT | GAAGCTTCAT | TCTTGGCATC | CATGGTCAAG | AACACTGGAA | ACAGCTACCA |
| 370 | 380 | 390 | 400 | 410 | 420 |
| ATATACCTGG | ATTGGACTCC | ATGACCCCAC | TCTTGGTGGA | GAACCCAATG | GAGGTGGATG |
| 430 | 440 | 450 | 460 | 470 | 480 |
| GGAGTGGAGT | AACAATGACA | TAATGAATTA | TGTCAACTGG | GAGAGGAACC | CATCTACTGC |
| 490 | 500 | 510 | 520 | 530 | 540 |
| CTTAGACCGC | GGATTCTGTG | GCAGCTTGTC | AAGATCTTCT | GGATTTCTAA | GATGGAGAGA |
| 550 | 560 | 570 | 580 | 590 | 600 |
| TACCACATGT | GAAGTTGAAG | TTGCCCTACG | TCTGCAAATT | TACAGGTTAA | AATTACCAGA |
| 610 | 620 | 630 | 640 | 650 | 660 |
| CAGCAAACAG | CTTTAGTTTG | TCCTGAAGCA | CATCCTGTCA | AGGGGCAAAA | TATGAAGACT |
| 670 | 680 | 690 | 700 | 710 | 720 |
| TGCGTAGAAA | AAGTGTATTC | TATCTACAGT | CCATATTGGA | GCTCTAATCA | TTCTTTAGCC |
| 730 | 740 | 750 | 760 | 770 | 780 |
| AATTTTGTAT | AAGTTGTGTC | CTCATGTCTT | GGAAAGCAGT | AATAAACCTC | AGTCTCTCTT |
| 790 | 800 | 810 | 820 | 830 | 840 |
| CGAAAAAAAA | AAA | | | | |

It is specified that the above abbreviations have the following meanings: 1×SSC=150 mM NaCl, 15 mM sodium citrate; 50×Denhardt=5 g Ficoll, 5 g polyvinylpyrrolidone, 5 g bovine serum albumin in 500 ml of water; SDS: sodium dodecylsulfate; EDTA: sodium ethylene diamine tetraacetate.

Polyclonal antibodies directed against the rat PAP are produced according to standard techniques; such antibodies have been described, for example, by Keim et al. (Clin. Physiol. Biochem., 4: 136–142 (1986)).

A cDNA fragment belonging to the first family of nucleic acids of the invention is also characterized in that it codes for a protein corresponding to one of the following amino acid sequences A1 (SEQ ID NO: 2) (amino acid sequence of the protein including the signal peptide) or A2 (SEQ ID NO: 3) (amino acid sequence of the mature protein) or for an amino acid sequence having from 40 to 80%, and preferably from 50 to 60% homology with at least one sequence of about 25 amino acids within the A1 (SEQ ID NO: 2) or A2 (SEQ ID NO: 3) sequences.

Sequence A1:

MetLeuHisArgLeuAlaPheProValMetSerTrpMetLeuLeuSerCysLeuMetLeuLeuSerGlnValGln
GlyGluAspSerProLysLysIleProSerAlaArgIleSerCysProLysGlySerGlnAlaTyrGlySerTyr
CysTyrAlaLeuPheGlnIleProGlnThrTrpPheAspAlaGluLeuAlaCysGlnLysArgProGluGlyHis
LeuValSerValLeuAsnValAlaGluAlaSerPheLeuAlaSerMetValLysAsnThrGlyAsnSerTyrGln
TyrThrTrpIleGlyLeuHisAspProThrLeuGlyGlyGluProAsnGlyGlyGlyTrpGluTrpSerAsnAsn
AspIleMetAsnTyrValAsnTrpGluArgAsnProSerThrAlaLeuAspArgGlyPheCysGlySerLeuSer
ArgSerSerGlyPheLeuArgTrpArgAspThrThrCysGluValGluValAlaLeuArgLeuGlnIleTyrArg
LeuLysLeuProAspSerLysGlnLeu

Sequence A2:

GluAspSerProLysLysIleProSerAlaArgIleSerCysProLysGlySerGlnAlaTyrGlySerTyr
CysTyrAlaLeuPheGlnIleProGlnThrTrpPheAspAlaGluLeuAlaCysGlnLysArgProGluGlyHis
LeuValSerValLeuAsnValAlaGluAlaSerPheLeuAlaSerMetValLysAsnThrGlyAsnSerTyrGln
TyrThrTrpIleGlyLeuHisAspProThrLeuGlyGlyGluProAsnGlyGlyGlyTrpGluTrpSerAsnAsn
AspIleMetAsnTyrValAsnTrpGluArgAsnProSerThrAlaLeuAspArgGlyPheCysGlySerLeuSer
ArgSerSerGlyPheLeuArgTrpArgAspThrThrCysGluValGluValAlaLeuArgLeuGlnIleTyrArg
LeuLysLeuProAspSerLysGlnLeu

A second family of DNA fragments according to the invention includes cDNA fragments of a human PAP protein, such as those obtained by the implementation of the following steps:

- an initial screening of a human pancreatic cDNA library, the said human cDNA being inserted into an appropriate cloning vector, comprising the hybridization with probes consisting of the cDNA of the rat PAP protein in a solution constituted by: 6×SSC, 5×Denhardt, 0.5% SDS, 10 mM EDTA, 200 µg of salmon sperm DNA for 18 hours at 68° C., followed by rinsing under the following conditions: 6×SSC, 0.1% SDS, twice for 15 minutes at 65° C.,
- the selection of the positive human cDNA clones which had hybridized during the screening with the cDNA of the rat PAP protein, such clones being called positive, a second screening with a cDNA sequence of a PSP protein under the above hybridization conditions with rinsing using 0.1×SSC, 0.1% SDS for 2 hours at 65° C., in order to remove the unspecific clones According to a useful embodiment of the invention, a cDNA fragment coding for the human PAP corresponds to the following S3 sequence (SEQ ID NO: 4):

|     |     |     |     |     |     |     |     |     |     |     | ATG | CTG |
| --- | --- | --- | --- | --- | --- | --- | --- | --- | --- | --- | --- | --- |
| CCT | CCC | ATG | GCC | CTG | CCC | AGT | GTA | TCT | TGG | ATG | CTG | CTT |
| TCC | TGC | CTC | ATG | CTG | CTG | TCT | CAG | GTT | CAA | GGT | GAA | GAA |
| CCC | CAG | AGG | GAA | CTG | CCC | TCT | GCA | CGG | ATC | CGC | TGT | CCC |
| AAA | GGC | TCC | AAG | GCC | TAT | GGC | TCC | CAC | TGC | TAT | GCC | TTG |
| TTT | TTG | TCA | CCA | AAA | TCC | TGG | ACA | GAT | GCA | GAT | CTG | GCC |
| TGC | CAG | AAG | CGG | CCC | TCT | GGA | AAC | CTG | GTG | TCT | GTG | CTC |
| AGT | GGG | GCT | GAG | GGA | TCC | TTC | GTG | TCC | TCC | CTG | GTG | AAG |
| AGC | ATT | GGT | AAC | AGC | TAC | TCA | TAC | GTC | TGG | ATT | GGG | CTC |
| CAT | GAC | CCC | ACA | CAG | GGC | ACC | GAG | CCC | AAT | GGA | GAA | GGT |
| TGG | GAG | TGG | AGT | AGC | AGT | GAT | GTG | ATG | AAT | TAC | TTT | GCA |
| TGG | GAG | AGA | AAT | CCC | TCC | ACC | ATC | TCA | AGC | CCC | GGC | CAC |
| TGT | GCG | AGC | CTG | TCG | AGA | AGC | ACA | GCA | TTT | CTG | AGG | TGG |
| AAA | GAT | TAT | AAC | TGT | AAT | GTG | AGG | TTA | CCC | TAT | GTC | TGC |
| AAA | GTT | CAC |     |     |     |     |     |     |     |     |     |     | of human PAP cDNA which had, nonetheless, hybridized with the rat PAP cDNA and the recovery of the clones which had not hybridized with the PSP cDNA, the recovery of the cDNA fragments from the positive clones obtained.

A particularly useful cloning vector which can be modified by the human cDNA for the construction of the human pancreatic cDNA library is the vector λgt10.

PSP is a protein which exhibits certain structural analogies with the rat PAP. This protein has been described by Giorgi et al., J. Clin. Invest. (1989), 84, 100–106.

The cDNA fragments thus defined are characteristic of the family of proteins which include the human PAP protein.

According to a particular embodiment of the invention, preferred cDNA fragments are those obtained by the implementation of the preceding steps supplemented by the following step, prior to the recovery of the cDNA fragments from the positive clones obtained: screening with the rat PAP cDNA under hybridization conditions such as those described above, with rinsing for 2 hours at 65° C..

The invention also relates to the S4 cDNA fragment (SEQ ID NO: 12) which contains the S3 sequence as well as the following DNA sequences (SEQ ID NOS: 4–5) corresponding to the NH2 and COOH termini, respectively, of the corresponding protein:

tgacgtagtgcaggagggaagtcagcagcctgtgtttggt
gtgcaactcatcatgggcatgagaccagtgtgaggactcaccctggaagaga
atattcgcttaattcccccaacctgaccacctcattcttatctttcttctgt
ttcttcctccccgctagtcatttcagtctcttcattttgtcatacggcctaa
ggctttaaagagcaataaaatttttagtctgcaaaaaaa According to another embodiment of the invention, the cDNA of the human PAP is characterized in that it codes for the protein corresponding to the following A3 amino acid sequence (SEQ ID NO: 7):

|     |     |     |     |     |     |     |     |     |     |     | Met | Leu |
| --- | --- | --- | --- | --- | --- | --- | --- | --- | --- | --- | --- | --- |
| Pro | Pro | Met | Ala | Leu | Pro | Ser | Val | Ser | Trp | Met | Leu | Leu |
| Ser | Cys | Leu | Met | Leu | Leu | Ser | Gln | Val | Gln | Gly | Glu | Glu |
| Pro | Gln | Arg | Glu | Leu | Pro | Ser | Ala | Arg | Ile | Arg | Cys | Pro |
| Lys | Gly | Ser | Lys | Ala | Tyr | Gly | Ser | His | Cys | Tyr | Ala | Leu |
| Phe | Leu | Ser | Pro | Lys | Ser | Trp | Thr | Asp | Ala | Asp | Leu | Ala |
| Cys | Gln | Lys | Arg | Pro | Ser | Gly | Asn | Leu | Val | Ser | Val | Leu |
| Ser | Gly | Ala | Glu | Gly | Ser | Phe | Val | Ser | Ser | Leu | Val | Lys |
| Ser | Ile | Gly | Asn | Ser | Tyr | Ser | Tyr | Val | Trp | Ile | Gly | Leu |
| His | Asp | Pro | Thr | Gln | Gly | Thr | Glu | Pro | Asn | Gly | Glu | Gly |
| Trp | Glu | Trp | Ser | Ser | Ser | Asp | Val | Met | Asn | Tyr | Phe | Ala |
| Trp | Glu | Arg | Asn | Pro | Ser | Thr | Ile | Ser | Ser | Pro | Gly | His |
| Cys | Ala | Ser | Leu | Ser | Arg | Ser | Thr | Ala | Phe | Leu | Arg | Trp |
| Lys | Asp | Tyr | Asn | Cys | Asn | Val | Arg | Leu | Pro | Tyr | Val | Cys |
| Lys | Val | His |     |     |     |     |     |     |     |     |     |     | protein.

According to another definition of the cDNA fragments of the second family, a cDNA fragment according to the invention is characterized in that it includes a nucleotide sequence exhibiting a homology of at least 60%, and preferably at least 70%, with at least one sequence of about 100 nucleotides comprised in the following S2 sequence (SEQ ID NO: 8) which is characteristic of the cDNA of the mature PAP of the rat, or in the S3 sequence given above and characteristic of a cDNA fragment of human PAP.

Sequence S2:

| 10 | 20 | 30 | 40 | 50 | 60 |
| --- | --- | --- | --- | --- | --- |
| GAAGACT | CTCCGAAGAA | AATACCCTCT | GCACGCATTA | GTTGCCCCAA | AGGCTCCCAG |
| 70 | 80 | 90 | 100 | 110 | 120 |
| GCATATGGCT | CCTACTGCTA | TGCCCTGTTT | CAGATACCAC | AGACCTGGTT | TGATGCAGAA |
| 130 | 140 | 150 | 160 | 170 | 180 |

Sequence S2:

| | | | | | |
|---|---|---|---|---|---|
| CTGGCCTGCC | AGAAGAGACC | TGAAGGACAC | CTTGTATCTG | TGCTCAATGT | AGCTGAAGCT |
| 190 | 200 | 210 | 220 | 230 | 240 |
| TCATTCTTGG | CATCCATGGT | CAAGAACACT | GGAAACAGCT | ACCAATATAC | CTGGATTGGA |
| 250 | 260 | 270 | 280 | 290 | 300 |
| CTCCATGACC | CCACTCTTGG | TGGAGAACCC | AATGGAGGTG | GATGGGAGTG | GAGTAACAAT |
| 310 | 320 | 330 | 340 | 350 | 360 |
| GACATAATGA | ATTATGTCAA | CTGGGAGAGG | AACCCATCTA | CTGCCTTAGA | CCGCGGATTC |
| 370 | 380 | 390 | 400 | 410 | 420 |
| TGTGGCAGCT | TGTCAAGATC | TTCTGGATTT | CTAAGATGGA | GAGATACCAC | ATGTGAAGTT |
| 430 | 440 | 450 | 460 | 470 | 480 |
| GAAGTTGCCC | TACGTCTGCA | AATTTACAGG | TTAAAATTAC | CAGACAGCAA | ACAGCTT |

The invention also relates to cDNA fragments coding for the human PAP which are characterized by their capacity to hybridize with the S1 nucleotide sequence which is characteristic of the cDNA of the rat PAP, and/or with the S2 nucleotide sequence which is characteristic of the cDNA of the mature PAP of the rat, in a hybridization solution containing 6×SSC, 5×Denhardt, 0.5% SDS, 10 mM EDTA, 200 μg of salmon sperm DNA for 18 hours at 68° C., followed by rinsing with a solution consisting of 6×SSC, 0.1% SDS, twice for 15 minutes at 65° C.

A particularly preferred cDNA fragment of the human PAP in the framework of the present application is characterized in that it includes the following nucleotide sequence (SEQ ID NO: 9):

| | | | | | |
|---|---|---|---|---|---|
| 10 | 20 | 30 | 40 | 50 | 60 |
| TTTGTTAAGG | ATTCCCTTGA | GAATTATGTA | AAAGTTTTAC | AAGAGTCCAT | CTCATTCTCT |
| 70 | 80 | 90 | 100 | 110 | 120 |
| TTGTCCCCCT | CAAAGCTGGC | TTGCCAGAAG | CGGCCCTCTG | GAAAACTGGT | GTCTGTGCTC |
| 130 | 140 | 150 | 160 | 170 | 180 |
| AGTGGGGCTG | AGGGATCCTT | CGTGTCCTCC | CTGGTGAGGA | GCATTAGTAA | CAGCTACTCA |
| 190 | 200 | 210 | 220 | 230 | 240 |
| TACATCTGGA | TTGGGCTCCA | TGACCCACA | CAGGTGCGAG | TATATCCTCC | CCTCTCTGTT |
| 250 | 260 | 270 | 290 | 290 | 300 |
| ACCTCTAAG | GTACTGTTGT | TGCCCAGGCG | CACTCCCTGT | CCCCAGTCCC | TGCCCAGGAA |
| GTACTT | | | | | |

The inventors have observed that the protein sequence deduced from this human nucleotide sequence exhibits certain homologies with the sequence coding for the rat PAP protein, although the only evidence up to now obtained from antibodies directed against the rat PAP did not enable the human PAP protein to be detected in a given biological sample.

The identification of a cDNA fragment coding for the human PAP protein now makes it possible to contemplate the production of this protein, in particular by means of genetic engineering, as well as the production of antibodies which can be used as diagnostic agents of acute pancreatitis.

The invention also relates to a nucleic acid fragment characterized in that it is a DNA fragment complementary to the cDNA fragments defined above, or also in that it is the RNA fragment corresponding to these cDNAs.

The invention also relates to any fragment of a nucleotide sequence coding for the human PAP which is capable of being used as a probe, after suitable labelling of the said fragment, for the purpose of developing a means to detect the nucleic acid characteristic of the human PAP in a biological sample.

The invention also relates to the human PAP protein as obtained by the expression of a cDNA fragment of the human PAP, such as that defined above, by means of a suitable system of expression, for example a cell host transformed by an expression vector, itself modified by the insertion of the above-mentioned cDNA fragment of the human PAP.

A special human PAP protein according to the invention is a protein such as that produced by the expression of a cDNA fragment of the human PAP, inserted in phase in a pEX vector, in E. coli, in particular in the E. coli strain pop2136.

Human PAP proteins according to the invention are also characterized in that their amino acid sequences exhibit a homology of at least 50%, and preferably at least 60% and in the most preferred case at least 70% of at least one sequence of about 25 amino acids included in the A2 sequence of the mature PAP protein of the rat, or in the A3 sequence of the human PAP protein described above.

According to a particular embodiment of the invention, the human PAP protein corresponds to the A3 sequence given on the preceding pages.

The invention also relates to any fragment of the A3 sequence provided that it is recognized by antibodies recognizing this sequence, in particular monoclonal antibodies directed specifically against the A3 sequence.

The human PAP protein may be produced by the procedures of genetic engineering or also by purification, for example by means of chromatography, starting from a biological sample containing it.

According to a particular specification of the invention, the human PAP protein corresponding to the foregoing specifications, comprises the following amino acid sequence (SEQ ID NO: 10):

| | | | | | | | | | | | | |
|---|---|---|---|---|---|---|---|---|---|---|---|---|
| | | | | | | | | | | | | 39 |
| Phe | Val | Lys | Asp | Ser | Leu | Glu | Asn | Tyr | Val | Lys | Val | Leu | 13 |
| | | | | | | | | | | | | 78 |
| Gln | Glu | Ser | Ile | Ser | Phe | Ser | Leu | Ser | Pro | Ser | Lys | Leu | 26 |

-continued

| | | | | | | | | | | | | 117 |
|---|---|---|---|---|---|---|---|---|---|---|---|---|
| Ala | Cys | Gln | Lys | Arg | Pro | Ser | Gly | Lys | Leu | Val | Ser | Val | 39 |
| | | | | | | | | | | | | 156 |
| Leu | Ser | Gly | Ala | Glu | Gly | Ser | Phe | Val | Ser | Ser | Leu | Val | 52 |
| | | | | | | | | | | | | 195 |
| Arg | Ser | Ile | Ser | Asn | Ser | Tyr | Ser | Tyr | Ile | Trp | Ile | Gly | 65 |
| | | | | | | | | | | | | 234 |
| Leu | His | Asp | Pro | Thr | Gln | Val | Arg | Val | Tyr | Pro | Pro | Leu | 78 |
| | | | | | | | | | | | | 273 |
| Ser | Val | Thr | Ser | Gln | Gly | Thr | Val | Val | Ala | Gln | Ala | His | 91 |
| | | | | | | | | | | | | 306 |
| Ser | Leu | Ser | Pro | Val | Pro | Ala | Gln | Glu | Val | Leu | | | 102 |

Also included in the framework of the present invention is the rat PAP protein characterized in that it corresponds to the A2 amino acid sequence (SEQ ID NO: 3) shown above, or to a variant or a part of this sequence provided that this part or this variant is recognized by antibodies directed against the rat PAP protein or in that it exhibits a homology of at least 50%, and preferably at least 60% with the above A2 sequence (SEQ ID NO: 3) of rat PAP, or with the A3 sequence (SEQ ID NO: 7) of the human PAP.

The invention also relates to the rat PAP protein corresponding to the A1 sequence (SEQ ID NO: 2) or to a variant of A1 exhibiting the characteristics defined above with respect to the A2 amino acid sequence (SEQ ID NO: 3).

In the rat the PAP is present in very low amounts in the normal human pancreas, and its synthesis may be considerably increased in the event of acute pancreatitis to a level about 50 to 100 times higher than that which prevails in the normal pancreas.

The level of the rat PAP protein undergoes an increase in the pancreatis juice at the time of acute pancreatic whereas the levels of the other enzymes diminish.

Furthermore, in pancreatitis all of the pancreatic secretory proteins escape into the blood. Consequently, the attempt to determine in the blood or in another biological sample of a human patient (for example urine or peritoneal fluid) the PAP protein whose synthesis is considerably increased in the event of pancreatitis, suggests that the normal/pathological differential will be much greater than that found in the tests usually used for detection, and hence it will be much easier to detect.

With this objective, the invention also relates to antibodies characterized in that they recognize the human PAP protein previously defined, and these antibodies may be either polyclonal or monoclonal.

Monoclonal antibodies are, for example, antibodies such as those produced by a hybridoma formed beforehand by fusion of a myeloma cell with a spleen cell of an animal previously immunized with a human PAP protein.

The invention also relates to the hybridomas formed by fusion of myeloma cells and spleen cells of an animal previously immunized with the human PAP protein, in particular with the protein corresponding to the A3 amino acid sequence.

Particularly useful monoclonal antibodies in the framework of the invention are those which recognize specifically the NH2-terminal portion of the human PAP. Particularly useful antibodies are further defined in that they recognize the human PAP and in that they show no immunological reaction with the other lectins.

As an example, a valuable monoclonal antibody, in particular for the detection of the human PAP (SEQ ID NO: 12), is a monoclonal antibody directed against the following peptide of the human PAP: Glu Glu Pro Gln Arg. In order to monitor this peptide in detection tests for the human PAP, a tyrosine residue has been added to the arginine, for example, so as to make labelling with iodine possible according to the usual labelling procedures.

The invention also relates to anti-idiotypic antibodies directed against the antigenic determinants of the antibodies of the invention which recognize the human PAP.

Other antibodies according to the invention are monoclonal antibodies which recognize the rat PAP protein.

A protocol for the immunization of selected animals, in particular mice and rabbits, for the implementation of the invention is the protocol described by Kohler and Milstein, Nature (1975), 256, 495–497.

Also included in the framework of the invention is an expression and/or cloning vector, characterized in that it comprises a DNA fragment selected from the previously defined fragments.

Particularly useful expression and/or cloning vectors for the implementation of the invention include the expression plasmid pEX which is capable of expressing the cDNA of the human PAP protein in a bacterium, for example E. coli.

Other vectors are selected as a function of the host in which they are to be expressed. In this respect, a vector of the baculovirus type may be used in the case of mammalian cells.

The invention also relates to a cell host transformed by an expression vector such as that previously defined under conditions leading to the production of the protein or peptide encoded by the DNA fragment of the invention, inserted in this vector.

As an example, cell hosts constituting a suitable expression system for the DNA fragments of the invention are bacteria such as E. coli, in particular the strain pop2136.

The invention also relates to the expression product of the cell host transformed in the manner just described.

Advantageously, the choice as to whether the DNA fragment according to the invention is expressed in a prokaryotic or eukaryotic host should be made as a function of the product desired, particularly in respect to its glycosylation.

As examples, useful cell hosts for the implementation of the invention are bacteria, for example E. coli, yeasts, insect or mammalian cells, for example CHO cells.

The present invention also relates to compositions, characterized in that they contain at least one antibody selected from those which have been previously defined, directed against the human PAP protein. Such a composition may be a composition for in vitro diagnosis, to be used on a biological sample such as blood, urine or the peritoneal fluid of a patient showing the symptoms of acute pancreatitis.

Where appropriate, the antibodies used will be labelled by suitable chemical markers.

The invention also relates to a kit for the in vitro diagnosis of acute pancreatitis in a defined biological sample, characterized in that it contains:
- at least one antibody selected from those previously described which are capable of detecting the presence of an antigen of the human PAP type in the said biological sample, the said antibodies being labelled,
- depending on the type of labelling, a reagent to detect the presence of a complex of a specific antigen-antibody type,
- a negative control.

Preferably, the antibodies used are specific for the human PAP if they show no reaction with the other known lectins.

In order to carry out the labelling of the antibodies according to the invention, recourse may be had for example to radioisotopes, to chemical or enzymatic markers, and to chemiluminescent markers.

Moreover, the invention relates to a procedure for the in vitro detection of acute pancreatitis starting from a biological sample and which comprises the following steps:
- placing of the biological sample likely to contain the human PAP in contact with antibodies directed against the human PAP,
- detection of the antigen-antibody reaction between the above-mentioned antibodies and the human PAP.

The invention also relates, where appropriate, to the use of the antibodies directed against the PAP in the form of a composition containing several labelled antibodies for visualization by medical imaging of the pancreas, the antibody being labelled beforehand by means of a radioisotope or a chemical or enzymatic marker. The visualization may permit the detection of the presence of human PAP.

In this connection, the invention relates to an observation procedure of the pancreas characterized by:
- the injection of a composition mentioned above into a patient under physiologically acceptable conditions,
- the observation of a reaction between the antibodies contained in the above-mentioned composition and the human PAP if it is present.

BRIEF DESCRIPTION OF THE DRAWINGS

Other characteristics and advantages of the invention will become apparent in the examples and the figures which follow:

FIG. 1: Expression of the PAP and amylase during experimental acute pancreatitis induced in the rat. Analysis by "Northern blot"—load per lane: 30 μg of total RNA, the same filter was used successively for PAP and amylase. Probes: PAP cDNA (about 800 bp) and amylase (about 1100 bp), labelled with $^{32}P$ with a specific activity of about $2 \times 10^9$ cpm/mg.

the following phenomena are observed: induction of the expression of the pap gene (12 hours–48 hours) (acute phase); suppression of the induction during recovery (5–10 days); on the other hand, the amylase falls during the acute phase.

FIG. 2: nucleotide sequence coding for the rat PAP, and the corresponding amino acid sequence (SEQ ID NO: 1).

FIG. 3: fragment of the nucleotide sequence (SEQ ID NO: 2) coding for the human PAP, and the corresponding amino acid sequence (SEQ ID NO: 9).

FIG. 4: nucleotide sequence (SEQ ID NO: 12) (S4) characteristic of the human PAP including the coding sequence S4 (SEQ ID NO: 4), and the sequence (SEQ ID NO: 7) of amino acids (A3) which corresponds to it.

1. Construction of a rat pancreatic cDNA library in the vector λgt11.

Preparation of rat pancreatic RNA: the preparation was carried out by following exactly the procedure of Chirgwin, J. M. et al., Biochemistry (WASH) (1979), 19, 5294–5299. The messenger RNA fraction of this total RNA was separated by chromatography on a column of oligo-dT cellulose according to the technique of Aviv, H. and Leder, P., Proc. Natl. Acad. Sci., USA, (1972), 69, 1408–1412.

Preparation of the cDNA: the pancreatic cDNA was synthesized with the aid of the kit marketed by Amersham France S.A. (code RPN 1256), by following exactly the directions of the manufacturer.

Construction of the library: the library was constructed in the expression vector λgt11 with the aid of the kit marketed by Amersham France S.A. (code RPN 1280), by following exactly the directions of the manufacturer.

2. Construction of a human pancreatic cDNA library in the vector λgt10.

Preparation of human pancreatic RNA and synthesis of the cDNA corresponding to the RNA messengers: fragments of normal pancreas obtained from organ donors who have undergone brain death were treated as described above for the rat pancreas.

Construction of the library: the library was constructed in the cloning vector λgt10 with the aid of the kit marketed by Amersham France S.A. (code RPN 1257), by following the directions of the manufacturer.

3. Screening of the human pancreatic cDNA library with a clone expressing the rat PAP.

Starting from the rat pancreatic cDNA library constructed according to the above method, a clone recognized by polyclonal antibodies directed against the rat PAP was selected.

The cDNA of this clone of rat PAP was isolated and used as a probe to screen the human pancreatic cDNA bank obtained in λgt10, as described above.

In the first stage, the screening was carried out under the following conditions of stringency: 6×SSC, 5×Denhardt, 0.5% SDS, 10 mM EDTA, 200 μg of salmon sperm DNA for 18 hours at 68° C., following by rinsing with 6×SSC, 0.1% SDS, twice for 15 minutes at 65° C. This procedure made it possible to obtain about 80 clones of human cDNA.

Subsequently a screening with the PSP cDNA was carried out for the purpose of removing the clones which were not characteristic of the human PAP but which were, nonetheless, capable of hybridizing with the cDNA of the rat PAP under the above conditions: about 50 clones were recovered which thus contained a cDNA fragment coding for a protein or a polypeptide belonging to the family of the human PAP protein.

From these clones those were selected whose cDNA exhibits a very strong homology with the rat PAP protein, by performing a second screening using the cDNA of rat PAP under the following conditions of stringency: 6×SSC, 5×Denhardt, 0.5% SDS, 10 mM EDTA, 200 μg of salmon sperm DNA for 18 hours at 68° C., followed by rinsing with 6×SSC, 0.1% SDS for 2 hours at 65° C. 9 positive clones were selected in this way.

4. Sequencing of the selected clones.

The inserts of the useful clones were subcloned in the phages M13mp18-M13mp19 as described in "Molecular Cloning, a laboratory manual", Sambrook, J. Fritsch, E. F., and Maniatis T. eds., Cold Spring Harbor Laboratory Press (1990). The sequencing of the recombinant M13 phages was performed by means of the procedure described by Sanger F. et al., Proc. NAtl. Acad. Sci. (USA) (1977), 74, 5463-5467, by using the universal primer marketed by Amersham (code N4511).

5. Expression of a fragment of PAP in *E. coli* with the aid of the expression plasmid pEX and preparation of antibodies against the hybrid protein.

An expression kit employing the plasmid pEX in *E. coli*, marketed by the Genofit company under the catalogue number G2104, was used by following the directions of the manufacturer. Restriction fragments corresponding to the sequence coding for the protein were inserted into the pEX plasmid. The recombinant plasmids served to transform bacteria (*E. coli* strain pop2136). The proteins of the recombinant bacteria were analysed by means of electrophoresis on a 7.5% polyacrylamide gel. The protein band corresponding to the hybrid PAP was excised, homogenised in Freund's adjuvant and injected into rabbits at a rate of 3 injections per rabbit at intervals of 3 weeks, each injection containing about 20 μg of hybrid protein. The blood of the rabbits was then collected and the G immunoglobulins were purified on a column of protein A-Sepharose (Pharmacia-France).

---

We claim:

1. A polyclonal antibody, characterized in that said antibody specifically binds a human pancreatitis associated protein (PAP) encoded by a cDNA fragment obtained by:
   (a) screening a human pancreatic cDNA library, said human cDNA being inserted into a suitable cloning vector, comprising the hybridization with probes comprising cDNA of rat PAP protein in a solution comprising 6×SSC, 5×Denhardt, 0.5% SDS, 10 mM EDTA, 200 µg of salmon sperm DNA for 18 hours at 68° C., followed by rinsing under the following conditions: 6×SSC, 0.1% SDS, twice for 15 minutes at 65° C.;
   (b) selecting positive clones of human cDNA which hybridized during said screening with the cDNA of said rat PAP protein, these clones being called positive;
   (c) screening with a cDNA sequence of a pancreatic stone protein (PSP) protein under the above conditions of hybridization, followed by rinsing with 0.1×SSC, 0.1% SDS for 2 hours at 65° C. in order to remove the unspecific clones of human PAP cDNA which had hybridized with the cDNA of rat PAP;
   (d) recovering clones which had not hybridized with the PSP cDNA; and
   (e) recovering cDNA fragments from the positive clones obtained in step (d).

2. The antibody of claim 1, characterized in that it specifically binds the $NH_2$-terminal portion of the amino acid sequence A3 (SEQ ID NO:7).

3. A composition for the in vitro screening of acute pancreatitis or for the observation of the pancreas by medical imaging, comprising the antibody of claim 1, which has been labelled.

4. A kit for the in vitro screening of acute pancreatitis, comprising:
   (a) an antibody of claim 1, which has been labelled,
   (b) a reagent for detecting a complex between human pancreatitis associated protein and said antibody; and (c) a negative control.

5. A method for in vitro screening of acute pancreatitis, comprising
   (a) contacting a biological sample with the antibody of claim 1, and
   (b) detecting any complex formed between said antibody and any human pancreatitis associated protein in said sample wherein the presence of human pancreatitis associated protein is indicative of acute pancreatitis.

* * * * *

UNITED STATES PATENT AND TRADEMARK OFFICE
CERTIFICATE OF CORRECTION

PATENT NO. : 5,436,169
DATED : July 25, 1995
INVENTOR(S) : Juan-Lucio IOVANNA, et al.

It is certified that error appears in the above-indentified patent and that said Letters Patent is hereby corrected as shown below:

On the title page, Item [54] and Column 1, Lines 2-4, the title should read:

--PROTEIN ASSOCIATED WITH ACUTE PANCREATITIS, AGENTS FOR THE SCREENING OF ACUTE PANCREATITIS--

On the title page, Item [75], the inventorship should read:

--Juan-Lucio Iovanna, Marseille, France; Volker Keim, Heddesheim, Germany; Jean-Charles Dagorn, Marseille, France--

Signed and Sealed this

Seventh Day of November, 1995

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 793 base pairs
        ( B ) TYPE: nucleic acid
        ( C ) STRANDEDNESS: unknown
        ( D ) TOPOLOGY: unknown ( i i ) MOLECULE TYPE: cDNA to mRNA ( v i ) ORIGINAL SOURCE:
        ( A ) ORGANISM: rat
        ( F ) TISSUE TYPE: pancreas ( i x ) FEATURE:
        ( A ) NAME/KEY: CDS
        ( B ) LOCATION: 62..613

( x i ) SEQUENCE DESCRIPTION: SEQ ID NO:1:

```
AAAACCATCC  AAATCGCCCG  CAAGACAGCT  AAGGAGGAGC  AGAAAGATGA  TGAGAGTTAA                60

T  ATG  TTG  CAT  CGC  TTG  GCC  TTC  CCA  GTC  ATG  TCC  TGG  ATG  CTG  CTC         106
   Met  Leu  His  Arg  Leu  Ala  Phe  Pro  Val  Met  Ser  Trp  Met  Leu  Leu
    1              5                   10                      15

TCC  TGC  CTG  ATG  CTC  TTA  TCA  CAG  GTG  CAA  GGA  GAA  GAC  TCT  CCG  AAG       154
Ser  Cys  Leu  Met  Leu  Leu  Ser  Gln  Val  Gln  Gly  Glu  Asp  Ser  Pro  Lys
              20                       25                      30

AAA  ATA  CCC  TCT  GCA  CGC  ATT  AGT  TGC  CCC  AAA  GGC  TCC  CAG  GCA  TAT       202
Lys  Ile  Pro  Ser  Ala  Arg  Ile  Ser  Cys  Pro  Lys  Gly  Ser  Gln  Ala  Tyr
                   35                        40                      45

GGC  TCC  TAC  TGC  TAT  GCC  CTG  TTT  CAG  ATA  CCA  CAG  ACC  TGG  TTT  GAT       250
Gly  Ser  Tyr  Cys  Tyr  Ala  Leu  Phe  Gln  Ile  Pro  Gln  Thr  Trp  Phe  Asp
         50                        55                       60

GCA  GAA  CTG  GCC  TGC  CAG  AAG  AGA  CCT  GAA  GGA  CAC  CTT  GTA  TCT  GTG       298
Ala  Glu  Leu  Ala  Cys  Gln  Lys  Arg  Pro  Glu  Gly  His  Leu  Val  Ser  Val
     65                        70                       75

CTC  AAT  GTA  GCT  GAA  GCT  TCA  TTC  TTG  GCA  TCC  ATG  GTC  AAG  AAC  ACT       346
Leu  Asn  Val  Ala  Glu  Ala  Ser  Phe  Leu  Ala  Ser  Met  Val  Lys  Asn  Thr
 80                        85                       90                       95
```

-continued

| | | | | | | | | | | | | | | | |
|---|---|---|---|---|---|---|---|---|---|---|---|---|---|---|---|
| GGA | AAC | AGC | TAC | CAA | TAT | ACC | TGG | ATT | GGA | CTC | CAT | GAC | CCC | ACT | CTT | 394 |
| Gly | Asn | Ser | Tyr | Gln 100 | Tyr | Thr | Trp | Ile 105 | Gly | Leu | His | Asp | Pro 110 | Thr | Leu |

| GGT | GGA | GAA | CCC | AAT | GGA | GGT | GGA | TGG | GAG | TGG | AGT | AAC | AAT | GAC | ATA | 442 |
| Gly | Gly | Glu | Pro 115 | Asn | Gly | Gly | Gly | Trp 120 | Glu | Trp | Ser | Asn | Asn 125 | Asp | Ile |

| ATG | AAT | TAT | GTC | AAC | TGG | GAG | AGG | AAC | CCA | TCT | ACT | GCC | TTA | GAC | CGC | 490 |
| Met | Asn | Tyr 130 | Val | Asn | Trp | Glu | Arg 135 | Asn | Pro | Ser | Thr | Ala 140 | Leu | Asp | Arg |

| GGA | TTC | TGT | GGC | AGC | TTG | TCA | AGA | TCT | TCT | GGA | TTT | CTA | AGA | TGG | AGA | 538 |
| Gly | Phe 145 | Cys | Gly | Ser | Leu | Ser 150 | Arg | Ser | Ser | Gly | Phe 155 | Leu | Arg | Trp | Arg |

| GAT | ACC | ACA | TGT | GAA | GTT | GAA | GTT | GCC | CTA | CGT | CTG | CAA | ATT | TAC | AGG | 586 |
| Asp 160 | Thr | Thr | Cys | Glu 165 | Val | Glu | Val | Ala | Leu 170 | Arg | Leu | Gln | Ile | Tyr 175 | Arg |

| TTA | AAA | TTA | CCA | GAC | AGC | AAA | CAG | CTT | TAGTTTGTCC | TGAAGCACAT | 633 |
| Leu | Lys | Leu | Pro | Asp 180 | Ser | Lys | Gln | Leu | | |

CCTGTCAAGG GGCAAAATAT GAAGACTTGC GTAGAAAAAG TGTATTCTAT CTACAGTCCA        693

TATTGGAGCT CTAATCATTC TTTAGCCAAT TTTGTATAAG TTGTGTCCTC ATGTCTTGGA        753

AAGCAGTAAT AAACCTCAGT CTCTCTTCGA AAAAAAAAAA        793

(2) INFORMATION FOR SEQ ID NO:2:

(i) SEQUENCE CHARACTERISTICS:
  (A) LENGTH: 184 amino acids
  (B) TYPE: amino acid
  (D) TOPOLOGY: linear (ii) MOLECULE TYPE: protein (xi) SEQUENCE DESCRIPTION: SEQ ID NO:2:

| Met 1 | Leu | His | Arg | Leu 5 | Ala | Phe | Pro | Val | Met 10 | Ser | Trp | Met | Leu | Ser 15 |
|---|---|---|---|---|---|---|---|---|---|---|---|---|---|---|
| Cys | Leu | Met | Leu 20 | Leu | Ser | Gln | Val | Gln 25 | Gly | Glu | Asp | Ser | Pro 30 | Lys | Lys |
| Ile | Pro | Ser 35 | Ala | Arg | Ile | Ser | Cys 40 | Pro | Lys | Gly | Ser | Gln 45 | Ala | Tyr | Gly |
| Ser | Tyr 50 | Cys | Tyr | Ala | Leu | Phe 55 | Gln | Ile | Pro | Gln | Thr 60 | Trp | Phe | Asp | Ala |
| Glu 65 | Leu | Ala | Cys | Gln | Lys 70 | Arg | Pro | Glu | Gly | His 75 | Leu | Val | Ser | Val | Leu 80 |
| Asn | Val | Ala | Glu | Ala 85 | Ser | Phe | Leu | Ala | Ser 90 | Met | Val | Lys | Asn | Thr 95 | Gly |
| Asn | Ser | Tyr | Gln 100 | Tyr | Thr | Trp | Ile | Gly 105 | Leu | His | Asp | Pro | Thr 110 | Leu | Gly |
| Gly | Glu | Pro | Asn 115 | Gly | Gly | Gly | Trp | Glu 120 | Trp | Ser | Asn | Asn | Asp 125 | Ile | Met |
| Asn | Tyr 130 | Val | Asn | Trp | Glu | Arg 135 | Asn | Pro | Ser | Thr | Ala 140 | Leu | Asp | Arg | Gly |
| Phe 145 | Cys | Gly | Ser | Leu | Ser 150 | Arg | Ser | Ser | Gly | Phe 155 | Leu | Arg | Trp | Arg | Asp 160 |
| Thr | Thr | Cys | Glu | Val 165 | Glu | Val | Ala | Leu | Arg 170 | Leu | Gln | Ile | Tyr | Arg 175 | Leu |
| Lys | Leu | Pro | Asp | Ser 180 | Lys | Gln | Leu |

(2) INFORMATION FOR SEQ ID NO:3:

(i) SEQUENCE CHARACTERISTICS:

(A) LENGTH: 158 amino acids
(B) TYPE: amino acid
(D) TOPOLOGY: unknown (ii) MOLECULE TYPE: protein (vi) ORIGINAL SOURCE:
   (A) ORGANISM: Homo sapiens
   (F) TISSUE TYPE: pancreas (xi) SEQUENCE DESCRIPTION: SEQ ID NO:3:

```
Glu Asp Ser Pro Lys Lys Ile Pro Ser Ala Arg Ile Ser Cys Pro Lys
1               5                   10                  15

Gly Ser Gln Ala Tyr Gly Ser Tyr Cys Tyr Ala Leu Phe Gln Ile Pro
                20                  25                  30

Gln Thr Trp Phe Asp Ala Glu Leu Ala Cys Gln Lys Arg Pro Glu Gly
            35                  40                  45

His Leu Val Ser Val Leu Asn Val Ala Glu Ala Ser Phe Leu Ala Ser
        50                  55                  60

Met Val Lys Asn Thr Gly Asn Ser Tyr Gln Tyr Thr Trp Ile Gly Leu
65                  70                  75                  80

His Asp Pro Thr Leu Gly Gly Glu Pro Asn Gly Gly Gly Trp Glu Trp
                85                  90                  95

Ser Asn Asn Asp Ile Met Asn Tyr Val Asn Trp Glu Arg Asn Pro Ser
                100                 105                 110

Thr Ala Leu Asp Arg Gly Phe Cys Gly Ser Leu Ser Arg Ser Ser Gly
            115                 120                 125

Phe Leu Arg Trp Arg Asp Thr Thr Cys Glu Val Glu Val Ala Leu Arg
130                 135                 140

Leu Gln Ile Tyr Arg Leu Lys Leu Pro Asp Ser Lys Gln Leu
145                 150                 155
```

(2) INFORMATION FOR SEQ ID NO:4:

(i) SEQUENCE CHARACTERISTICS:
      (A) LENGTH: 522 base pairs
      (B) TYPE: nucleic acid
      (C) STRANDEDNESS: unknown
      (D) TOPOLOGY: unknown (ii) MOLECULE TYPE: cDNA (vi) ORIGINAL SOURCE:
      (A) ORGANISM: Homo sapiens
      (F) TISSUE TYPE: pancreas (xi) SEQUENCE DESCRIPTION: SEQ ID NO:4:

```
ATGCTGCCTC CCATGGCCCT GCCCAGTGTA TCTTGGATGC TGCTTTCCTG CCTCATGCTG      60
CTGTCTCAGG TTCAAGGTGA AGAACCCCAG AGGGAACTGC CCTCTGCACG GATCCGCTGT     120
CCCAAAGGCT CCAAGGCCTA TGGCTCCCAC TGCTATGCCT TGTTTTTGTC ACCAAAATCC     180
TGGACAGATG CAGATCTGGC CTGCCAGAAG CGGCCCTCTG GAAACCTGGT GTCTGTGCTC     240
AGTGGGGCTG AGGGATCCTT CGTGTCCTCC CTGGTGAAGA GCATTGGTAA CAGCTACTCA     300
TACGTCTGGA TTGGGCTCCA TGACCCCACA CAGGGCACCG AGCCCAATGG AGAAGGTTGG     360
GAGTGGAGTA GCAGTGATGT GATGAATTAC TTTGCATGGG AGAGAAATCC CTCCACCATC     420
TCAAGCCCCG GCCACTGTGC GAGCCTGTCG AGAAGCACAG CATTTCTGAG GTGGAAAGAT     480
TATAACTGTA ATGTGAGGTT ACCCTATGTC TGCAAAGTTC AC                        522
```

(2) INFORMATION FOR SEQ ID NO:5:

(i) SEQUENCE CHARACTERISTICS:
      (A) LENGTH: 42 base pairs (B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Homo sapiens
(D) DEVELOPMENTAL STAGE: pancreas (xi) SEQUENCE DESCRIPTION: SEQ ID NO:5:

```
CGGGAGAGTG ACTCCTGATT GCCTCCTCAA GTCGCAGACA CT                    42
```

(2) INFORMATION FOR SEQ ID NO:6:

(i) SEQUENCE CHARACTERISTICS:
(A) LENGTH: 234 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Homo sapiens
(F) TISSUE TYPE: pancreas (xi) SEQUENCE DESCRIPTION: SEQ ID NO:6:

```
TGACTAGTGC AGGAGGGAAG TCAGCAGCCT GTGTTTGGTG TGCAACTCAT CATGGGCATG    60
AGACCAGTGT GAGGACTCAC CCTGGAAGAG AATATTCGCT TAATTCCCCC AACCTGACCA   120
CCTCATTCTT ATCTTTCTTC TGTTTCTTCC TCCCCGCTAG TCATTTCAGT CTCTTCATTT   180
TGTCATACGG CCTAAGGCTT TAAAGAGCAA TAAAATTTTT AGTCTGCAAA AAAA         234
```

(2) INFORMATION FOR SEQ ID NO:7:

(i) SEQUENCE CHARACTERISTICS:
(A) LENGTH: 174 amino acids
(B) TYPE: amino acid
(D) TOPOLOGY: unknown (ii) MOLECULE TYPE: protein (vi) ORIGINAL SOURCE:
(A) ORGANISM: Homo sapiens
(F) TISSUE TYPE: pancreas (xi) SEQUENCE DESCRIPTION: SEQ ID NO:7:

```
Met Leu Pro Pro Met Ala Leu Pro Ser Val Ser Trp Met Leu Leu Ser
 1               5                  10                  15

Cys Leu Met Leu Leu Ser Gln Val Gln Gly Glu Glu Pro Gln Arg Glu
             20                  25                  30

Leu Pro Ser Ala Arg Ile Arg Cys Pro Lys Gly Ser Lys Ala Tyr Gly
             35                  40                  45

Ser His Cys Tyr Ala Leu Phe Leu Ser Pro Lys Ser Trp Thr Asp Ala
     50                  55                  60

Asp Leu Ala Cys Gln Lys Arg Pro Ser Gly Asn Leu Val Ser Val Leu
 65                  70                  75                  80

Ser Gly Ala Glu Gly Ser Phe Val Ser Leu Val Lys Ser Ile Gly
                 85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
             115                 120                 125

Asn Tyr Phe Ala Trp Glu Arg Asn Pro Ser Thr Ile Ser Ser Pro Gly
 130                 135                 140
```

His Cys Ala Ser Leu Ser Arg Ser Thr Ala Phe Leu Arg Trp Lys Asp
                145                 150                 155                 160

Tyr Asn Cys Asn Val Arg Leu Pro Tyr Val Cys Lys Val His
                                165                 170

( 2 ) INFORMATION FOR SEQ ID NO:8:

( i ) SEQUENCE CHARACTERISTICS:
        ( A ) LENGTH: 474 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: rat
        ( F ) TISSUE TYPE: pancreas ( x i ) SEQUENCE DESCRIPTION: SEQ ID NO:8:

| | | | | | |
|---|---|---|---|---|---|
| GAAGACTCTC | CGAAGAAAAT | ACCCTCTGCA | CGCATTAGTT | GCCCCAAAGG | CTCCCAGGCA | 60 |
| TATGGCTCCT | ACTGCTATGC | CCTGTTTCAG | ATACCACAGA | CCTGGTTTGA | TGCAGAACTG | 120 |
| GCCTGCCAGA | AGAGACCTGA | AGGACACCTT | GTATCTGTGC | TCAATGTAGC | TGAAGCTTCA | 180 |
| TTCTTGGCAT | CCATGGTCAA | GAACACTGGA | AACAGCTACC | AATATACCTG | GATTGGACTC | 240 |
| CATGACCCCA | CTCTTGGTGG | AGAACCCAAT | GGAGGTGGAT | GGGAGTGGAG | TAACAATGAC | 300 |
| ATAATGAATT | ATGTCAACTG | GGAGAGGAAC | CCATCTACTG | CCTTAGACCG | CGGATTCTGT | 360 |
| GGCAGCTTGT | CAAGATCTTC | TGGATTTCTA | AGATGGAGAG | ATACCACATG | TGAAGTTGAA | 420 |
| GTTGCCCTAC | GTCTGCAAAT | TTACAGGTTA | AAATTACCAG | ACAGCAAACA | GCTT | 474 |

( 2 ) INFORMATION FOR SEQ ID NO:9:

( i ) SEQUENCE CHARACTERISTICS:
        ( A ) LENGTH: 306 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Homo sapiens
        ( F ) TISSUE TYPE: pancreas ( x i ) SEQUENCE DESCRIPTION: SEQ ID NO:9:

| | | | | | |
|---|---|---|---|---|---|
| TTTGTTAAGG | ATTCCCTTGA | GAATTATGTA | AAAGTTTTAC | AAGAGTCCAT | CTCATTCTCT | 60 |
| TTGTCCCCCT | CAAAGCTGGC | TTGCCAGAAG | CGGCCCTCTG | GAAAACTGGT | GTCTGTGCTC | 120 |
| AGTGGGGCTG | AGGGATCCTT | CGTGTCCTCC | CTGGTGAGGA | GCATTAGTAA | CAGCTACTCA | 180 |
| TACATCTGGA | TTGGGCTCCA | TGACCCCACA | CAGGTGCGAG | TATATCCTCC | CCTCTCTGTT | 240 |
| ACCTCTCAAG | GTACTGTTGT | TGCCCAGGCG | CACTCCCTGT | CCCCAGTCCC | TGCCCAGGAA | 300 |
| GTACTT | | | | | | 306 |

( 2 ) INFORMATION FOR SEQ ID NO:10:

( i ) SEQUENCE CHARACTERISTICS:
        ( A ) LENGTH: 102 amino acids
        ( B ) TYPE: amino acid
        ( D ) TOPOLOGY: unknown ( i i ) MOLECULE TYPE: protein ( v i ) ORIGINAL SOURCE:
        ( A ) ORGANISM: Homo sapiens
        ( F ) TISSUE TYPE: pancreas ( x i ) SEQUENCE DESCRIPTION: SEQ ID NO:10:

| Phe | Val | Lys | Asp | Ser | Leu | Glu | Asn | Tyr | Val | Lys | Val | Leu | Gln | Glu | Ser |
|---|---|---|---|---|---|---|---|---|---|---|---|---|---|---|---|
| 1 | | | | 5 | | | | | 10 | | | | | 15 | |

| Ile | Ser | Phe | Ser | Leu | Ser | Pro | Ser | Lys | Leu | Ala | Cys | Gln | Lys | Arg | Pro |
|---|---|---|---|---|---|---|---|---|---|---|---|---|---|---|---|
| | | | 20 | | | | | 25 | | | | | 30 | | |

| Ser | Gly | Lys | Leu | Val | Ser | Val | Leu | Ser | Gly | Ala | Glu | Gly | Ser | Phe | Val |
|---|---|---|---|---|---|---|---|---|---|---|---|---|---|---|---|
| | | | 35 | | | | | 40 | | | | | 45 | | |

| Ser | Ser | Leu | Val | Arg | Ser | Ile | Ser | Asn | Ser | Tyr | Ser | Tyr | Ile | Trp | Ile |
|---|---|---|---|---|---|---|---|---|---|---|---|---|---|---|---|
| | 50 | | | | | 55 | | | | | 60 | | | | |

| Gly | Leu | His | Asp | Pro | Thr | Gln | Val | Arg | Val | Tyr | Pro | Pro | Leu | Ser | Val |
|---|---|---|---|---|---|---|---|---|---|---|---|---|---|---|---|
| 65 | | | | | 70 | | | | | 75 | | | | | 80 |

| Thr | Ser | Gln | Gly | Thr | Val | Val | Ala | Gln | Ala | His | Ser | Leu | Ser | Pro | Val |
|---|---|---|---|---|---|---|---|---|---|---|---|---|---|---|---|
| | | | | 85 | | | | | 90 | | | | | 95 | |

| Pro | Ala | Gln | Glu | Val | Leu |
|---|---|---|---|---|---|
| | | | 100 | | |

( 2 ) INFORMATION FOR SEQ ID NO:11:

( i ) SEQUENCE CHARACTERISTICS:
( A ) LENGTH: 5 amino acids
( B ) TYPE: amino acid
( D ) TOPOLOGY: unknown ( i i ) MOLECULE TYPE: protein ( v i ) ORIGINAL SOURCE:
( A ) ORGANISM: Homo sapiens
( F ) TISSUE TYPE: pancreas ( x i ) SEQUENCE DESCRIPTION: SEQ ID NO:11:

| Glu | Glu | Pro | Gln | Arg |
|---|---|---|---|---|
| 1 | | | | 5 |

( 2 ) INFORMATION FOR SEQ ID NO:12:

( i ) SEQUENCE CHARACTERISTICS:
( A ) LENGTH: 798 base pairs
( B ) TYPE: nucleic acid
( C ) STRANDEDNESS: unknown
( D ) TOPOLOGY: unknown ( i i ) MOLECULE TYPE: cDNA ( v i ) ORIGINAL SOURCE:
( A ) ORGANISM: Homo sapiens
( F ) TISSUE TYPE: pancreas ( x i ) SEQUENCE DESCRIPTION: SEQ ID NO:12:

```
CGGGAGAGTG ACTCCTGATT GCCTCCTCAA GTCGCAGACA CTATGCTGCC TCCCATGGCC    60
CTGCCCAGTG TATCTTGGAT GCTGCTTTCC TGCCTCATGC TGCTGTCTCA GGTTCAAGGT   120
GAAGAACCCC AGAGGGAACT GCCCTCTGCA CGGATCCGCT GTCCCAAAGG CTCCAAGGCC   180
TATGGCTCCC ACTGCTATGC CTTGTTTTTG TCACCAAAAT CCTGGACAGA TGCAGATCTG   240
GCCTGCCAGA AGCGGCCCTC TGGAAACCTG GTGTCTGTGC TCAGTGGGGC TGAGGGATCC   300
TTCGTGTCCT CCCTGGTGAA GAGCATTGGT AACAGCTACT CATACGTCTG GATTGGGCTC   360
CATGACCCCA CACAGGGCAC CGAGCCCAAT GGAGAAGGTT GGGAGTGGAG TAGCAGTGAT   420
GTGATGAATT ACTTTGCATG GGAGAGAAAT CCCTCCACCA TCTCAAGCCC CGGCCACTGT   480
GCGAGCCTGT CGAGAAGCAC AGCATTTCTG AGGTGGAAAG ATTATAACTG TAATGTGAGG   540
TTACCCTATG TCTGCAAAGT TCACTGACTA GTGCAGGAGG AAGTCAGCA GCCTGTGTTT   600
GGTGTGCAAC TCATCATGGG CATGAGACCA GTGTGAGGAC TCACCCTGGA AGAGAATATT   660
CGCTTAATTC CCCCAACCTG ACCACCTCAT TCTTATCTTT CTTCTGTTTC TTCCTCCCCG   720
```

```
CTAGTCATTT  CAGTCTCTTC  ATTTTGTCAT  ACGGCCTAAG  GCTTTAAAGA  GCAATAAAAT        780
TTTTAGTCTG  CAAAAAAA                                                          798
```